US008529592B2

(12) United States Patent
Yamada

(10) Patent No.: US 8,529,592 B2
(45) Date of Patent: Sep. 10, 2013

(54) ULTRASONIC OPERATING APPARATUS

(75) Inventor: Norihiro Yamada, Tokyo (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 13/408,128

(22) Filed: Feb. 29, 2012

(65) Prior Publication Data
US 2012/0221030 A1 Aug. 30, 2012

Related U.S. Application Data

(63) Continuation of application No. 12/035,716, filed on Feb. 22, 2008, now abandoned.

(51) Int. Cl.
*A61B 17/32* (2006.01)
(52) U.S. Cl.
USPC ........................................................ 606/169
(58) Field of Classification Search
USPC ................... 433/86, 117, 118, 119; 604/22;
606/37, 39, 40, 45, 49, 169, 170, 171
See application file for complete search history.

(56) References Cited

U.S. PATENT DOCUMENTS

| | | | | |
|---|---|---|---|---|
| 4,838,853 A | * | 6/1989 | Parisi ............................. | 604/22 |
| 4,979,952 A | * | 12/1990 | Kubota et al. ................. | 606/169 |
| 5,391,144 A | * | 2/1995 | Sakurai et al. ................. | 604/22 |
| 5,649,935 A | * | 7/1997 | Kremer et al. ................. | 606/128 |
| 5,688,235 A | * | 11/1997 | Sakurai et al. .................. | 604/22 |
| 5,873,873 A | * | 2/1999 | Smith et al. ........................ | 606/1 |
| 5,897,569 A | * | 4/1999 | Kellogg et al. ................ | 606/169 |
| 5,944,737 A | * | 8/1999 | Tsonton et al. ................. | 606/205 |
| 5,980,510 A | * | 11/1999 | Tsonton et al. .................... | 606/1 |
| 6,416,486 B1 | * | 7/2002 | Wampler ........................... | 601/2 |

(Continued)

FOREIGN PATENT DOCUMENTS

| | | | |
|---|---|---|---|
| DE | 3625749 A1 | * | 2/1987 |
| JP | 2-051523 | | 4/1990 |
| WO | WO 2006-048966 | | 5/2006 |

OTHER PUBLICATIONS

Office Action issued by the Japanese Patent Office on Jan. 8, 2013 in connection with corresponding Japanese Patent Application No. 2011-055788.

(Continued)

*Primary Examiner* — Ryan Severson
*Assistant Examiner* — Jonathan W Miles
(74) *Attorney, Agent, or Firm* — Ostrolenk Faber LLP

(57) ABSTRACT

An ultrasonic treatment instrument includes a piezoelectric element assembly, a probe, a backing plate, an electrode assembly, a cylinder and a cylindrical inner cover. The piezoelectric element assembly includes piezoelectric elements and generates ultrasonic vibration. The probe is connected to the piezoelectric element assembly and transmits the ultrasonic vibration. The backing plate is connected to the piezoelectric element assembly. The electrode assembly includes electrodes respectively clamped between the piezoelectric elements, electrifies the piezoelectric elements and generates the ultrasonic vibration. The cylinder is connected to the probe and locates the piezoelectric element assembly, the backing plate and the electrode assembly therein. The cylindrical inner cover includes an inner diameter larger than the backing plate and an outer diameter smaller than the cylinder. The inner cover is disposed between the backing plate and the electrode assembly, and the electrode assembly is disposed between the cylinder and the inner cover.

3 Claims, 11 Drawing Sheets

(56) References Cited

U.S. PATENT DOCUMENTS

| | | | |
|---|---|---|---|
| 7,172,420 B2* | 2/2007 | Huguenin et al. | 433/119 |
| 7,494,468 B2* | 2/2009 | Rabiner et al. | 600/459 |
| 2001/0001123 A1* | 5/2001 | Madan et al. | 606/169 |
| 2002/0002379 A1* | 1/2002 | Bishop | 606/169 |
| 2004/0170944 A1* | 9/2004 | Huguenin et al. | 433/119 |
| 2005/0027310 A1* | 2/2005 | Yamada et al. | 606/169 |
| 2009/0143796 A1* | 6/2009 | Stulen et al. | 606/169 |
| 2009/0299395 A1* | 12/2009 | Hirai et al. | 606/169 |

OTHER PUBLICATIONS

Translation of Office Action issued by the Japanese Patent Office on Jan. 8, 2013 in connection with corresponding Japanese Patent Application No. 2011-055788.

\* cited by examiner

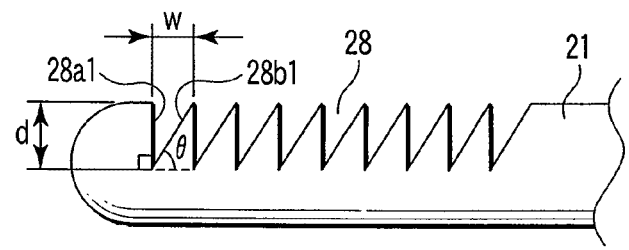
F I G. 6
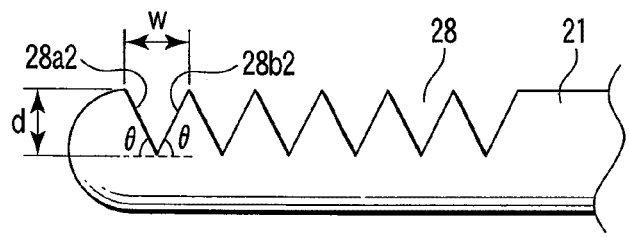
F I G. 7
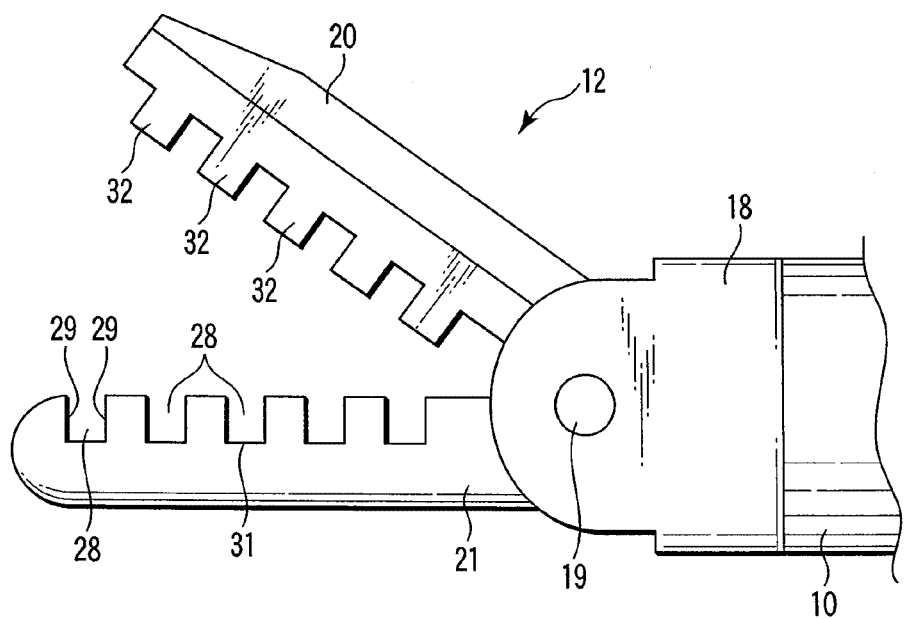
F I G. 8

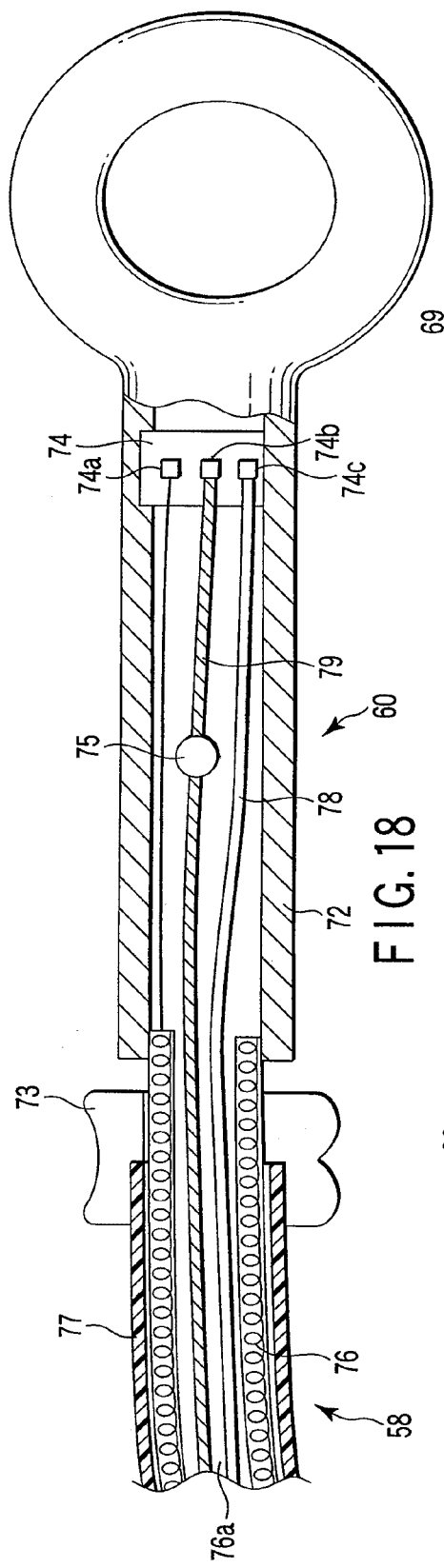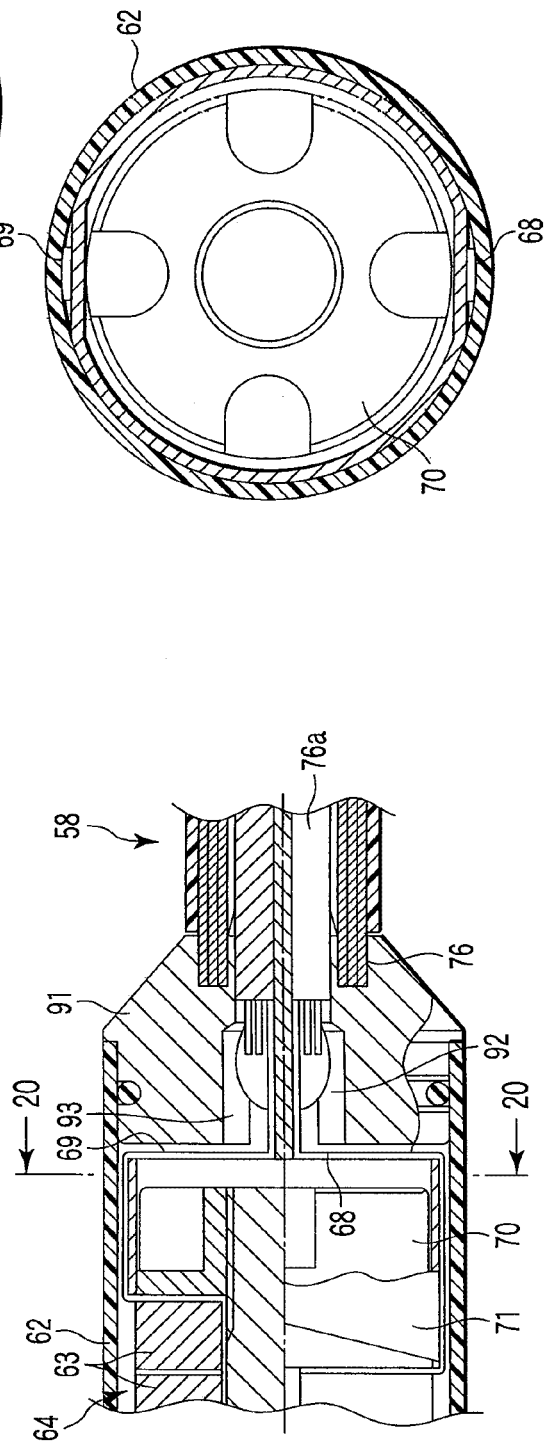

ULTRASONIC OPERATING APPARATUS

CROSS-REFERENCE TO RELATED APPLICATION

This application is a continuation of U.S. application Ser. No. 12/035,716, filed Feb. 22, 2008, by Norihiro YAMADA entitled ULTRASONIC OPERATING APPARATUS, the entire contents of which are incorporated herein by reference.

BACKGROUND OF THE INVENTION

The present invention relates to an ultrasonic treatment instrument which performs a procedure such as incising, removing, or clotting of a body tissue using ultrasonic waves.

As one example of an ordinary ultrasonic treatment instrument which performs a procedure such as incising, removing, or clotting of a body tissue by using ultrasonic waves, there is an ultrasonic clotting and incising apparatus disclosed in U.S. Pat. No. 5,980,510 (Patent Document 1). In the apparatus, a proximal end portion of an elongated insertion unit is coupled with an operation unit on a near side of an operator. An ultrasonic transducer for producing ultrasonic vibration is disposed in the operation unit. A procedure unit for treating a body tissue is disposed at a distal end portion of the insertion unit.

The insertion unit includes an elongated circular tube sheath. A rod-like vibration transmission member (probe) is inserted into the sheath. A proximal end portion of the vibration transmission member is detachably connected to an ultrasonic transducer via a connection unit of a screwing type. Ultrasonic vibration produced by the ultrasonic transducer is transmitted to a cylindrical probe distal end portion at a distal end side of the vibration transmission member.

A clamp arm is disposed in the procedure unit so as to face the probe distal end portion. A pad with uneven is fixed to the clamp arm. Here, an arm holding member for holding the clamp arm is provided at a distal end portion of the sheath of the insertion unit. A proximal end portion of the clamp arm is rotatably supported by the arm holding member via a supporting shaft. An operation member which drives the clamp arm is inserted into the sheath so as to be capable of advancing and retreating in an axial direction. An operation handle is disposed on the operation unit. The operation member is driven so as to advance and retreat in the axial direction according to operation of the operation handle. The clamp arm is operated to be opened or closed to the probe distal end portion in a linking manner with action of the operation member.

A body tissue is grasped between the cylindrical probe distal end portion and the pad of the clamp arm at a time of closing operation of the clamp arm. In this state, ultrasonic vibration from the ultrasonic transducer is transmitted to the probe distal end portion at the procedure unit side via the vibration transmission member so that a procedure such as incising, removing, or clotting of a body tissue is performed using ultrasonic waves.

U.S. Pat. No. 6,280,407 (Patent Document 2) discloses an ultrasonic clotting and incising apparatus where a procedure face of a distal end of an ultrasonic transmission member is inclined to an axial direction of a center axis of the ultrasonic transmission member by an angle of 15 to 70°.

BRIEF SUMMARY OF THE INVENTION

According to a first aspect of the present invention, an ultrasonic treatment instrument comprising: an ultrasonic transducer which produces ultrasonic vibration; a probe portion which has a distal end portion and a proximal end portion, the proximal end portion being coupled to the ultrasonic transducer, and ultrasonic wave outputted from the ultrasonic transducer is transmitted; a sheath portion which is formed from a cylinder body having a distal end portion and a proximal end portion and in which the probe portion is inserted detachably, the sheath portion having, at the distal end portion, a grasping member rotatably supported so as to face the probe portion; and a handle portion which is detachably coupled to the proximal end portion of the sheath portion and operates the grasping member such that the grasping member is opened and closed to the probe portion, wherein the distal end portion of the probe portion includes a cavitation production portion where the distal end portion of the probe portion has, on a face thereof facing the grasping member, a flat portion extending so as to intersect a vibration direction of the ultrasonic vibration, and cavitation is produced by the flat face in a state that a body tissue has been grasped between the grasping member and the distal end portion of the probe portion.

Preferably, the cavitation production portion includes a groove portion with an uneven shape on a face facing the grasping member at the distal end portion of the probe portion.

Preferably, the grasping member includes a fitting portion fitted to the groove portion at the distal end portion of the probe portion.

Preferably, the groove portion has a flat face provided so as to extend in a direction intersecting the vibration direction of the ultrasonic vibration at an angle of 70° to 90°.

Preferably, a plurality of the groove portions is formed on the face facing the grasping member at the distal end portion of the probe portion, and when one wavelength of the ultrasonic vibration is represented as $\lambda$, all the groove portions fall within a range from a distal end of the probe portion to $\lambda/8$.

Preferably, a width (w) of the groove portion extending along an axial direction of the probe portion is set so as to fall within a range of $\lambda/200 \leq w \leq \lambda/16$.

Preferably, the groove portion has a ratio (d/w) of a groove width (w) extending along an axial direction of the probe portion and a depth (d) is set to fall within a range of $0.1 \leq d/w \leq 5$.

According to another aspect of the present invention, an ultrasonic treatment instrument comprising: a flexible pipe portion having a distal end portion and a proximal end portion; a procedure tool main body disposed at the distal end portion of the flexible pipe portion; and a procedure tool operation unit disposed at the proximal end portion of the flexible pipe portion, wherein the procedure tool main body comprises: an ultrasonic transducer producing ultrasonic vibration, a cover member having a distal end portion and a proximal end portion and covering a periphery of the ultrasonic transducer, the proximal end portion of the cover member being fixed to the ultrasonic transducer, and a grasping member pivoted to the distal end portion of the cover member, and including a grasping face grasping a body tissue between the one and a distal end portion of the ultrasonic transducer at a position facing the distal end portion of the ultrasonic transducer; and the procedure tool operation unit comprises: a slide mechanism which has a distal end portion and a proximal end portion and whose distal end portion is coupled to the grasping member, and a handle portion which operates the grasping member such that the grasping member is opened and closed to the distal end portion of the ultrasonic transducer according to operation of the slide mechanism in an axial direction thereof, wherein the distal end portion of the ultrasonic transducer includes a cavitation production portion where the distal end portion of the ultrasonic transducer has, on a face thereof facing the grasping member, a flat portion extending so as to intersect a vibration direction of the ultrasonic vibration, and cavitation is produced by the flat face in a state that a body tissue has been grasped between the grasping member and the distal end portion of the ultrasonic transducer.

Preferably, the slide mechanism includes a distal end cover coupled to the grasping member, and an outer diameter of the distal end cover is smaller than an inner diameter of a channel of an endoscope in which the procedure tool main body is inserted.

Preferably, the slide mechanism includes a distal end portion and a proximal end portion, the distal end portion of the slide mechanism including an operation wire coupled to the grasping member.

Preferably, the cavitation production portion includes a groove portion with an uneven shape formed on a face facing the grasping face of the grasping member at the distal end portion of the ultrasonic transducer.

Preferably, the ultrasonic transducer has an entire length which is half the wavelength of ultrasonic vibration, and the ultrasonic transducer is fixed to the cover member at a node position of ultrasonic vibration of a quarter wavelength from a distal end portion of the ultrasonic transducer.

Preferably, the ultrasonic transducer comprises: a piezoelectric device stacked body comprising a plurality of piezoelectric devices, a horn expanding vibration amplitude of the piezoelectric device stacked body, plus and minus electrodes supplying power to the piezoelectric devices, a backing plate sandwiching the piezoelectric devices and the electrodes between the one and the horn and positioned at a rear end of the piezoelectric device stacked body, and an inner cover disposed between the plus and minus electrodes and the backing plate, wherein the inner cover has an inner diameter larger than the backing plate and an entire length longer than the backing plate, and has an outer diameter smaller than an inner diameter of the cover member.

Preferably, the flexible pipe portion includes a coil shaft having a diameter smaller than that of the cover member, and the backing plate has a taper with a smooth inclined face at a connecting portion with the coil shaft.

Preferably, the ultrasonic transducer produces ultrasonic vibration with a frequency of 100±25 kHz.

Preferably, the coil shaft is provided with an insulating outer tube covering an outer periphery of the coil shaft, a wire supplying power to the ultrasonic transducer is inserted into the coil shaft, and the coil shaft is electrically grounded.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a side view showing a first modification example of the distal end portion of the ultrasonic transmission member of the ultrasonic clotting and incising apparatus according to the first embodiment;

FIG. 7 is a side view showing a second modification example of the distal end portion of the ultrasonic transmission member of the ultrasonic clotting and incising apparatus according to the first embodiment;

FIG. 8 is a side view showing a peripheral portion of a distal end acting unit of an ultrasonic clotting and incising apparatus according to a second embodiment of the present invention in an enlarged manner;

FIG. 14 is a vertical sectional view of a main portion showing a state that the ultrasonic clotting and incising apparatus according to the third embodiment has been inserted into a channel of an endo scope;

FIG. 18 is a vertical sectional view showing a portion of an operation unit of the ultrasonic clotting and incising apparatus according to the third embodiment;

FIG. 19 is a vertical sectional view showing the peripheral portion of the distal end acting unit of the ultrasonic clotting and incising apparatus according to the third embodiment;

FIG. 20 is a sectional view taken along line 20-20 in FIG. 19;

FIG. 23 is a side view showing a state that the grasping member of the second modification example of the distal end acting unit of the ultrasonic clotting and incising apparatus according to the third embodiment has been operated to be opened;

DETAILED DESCRIPTION OF THE INVENTION

Figure 1:
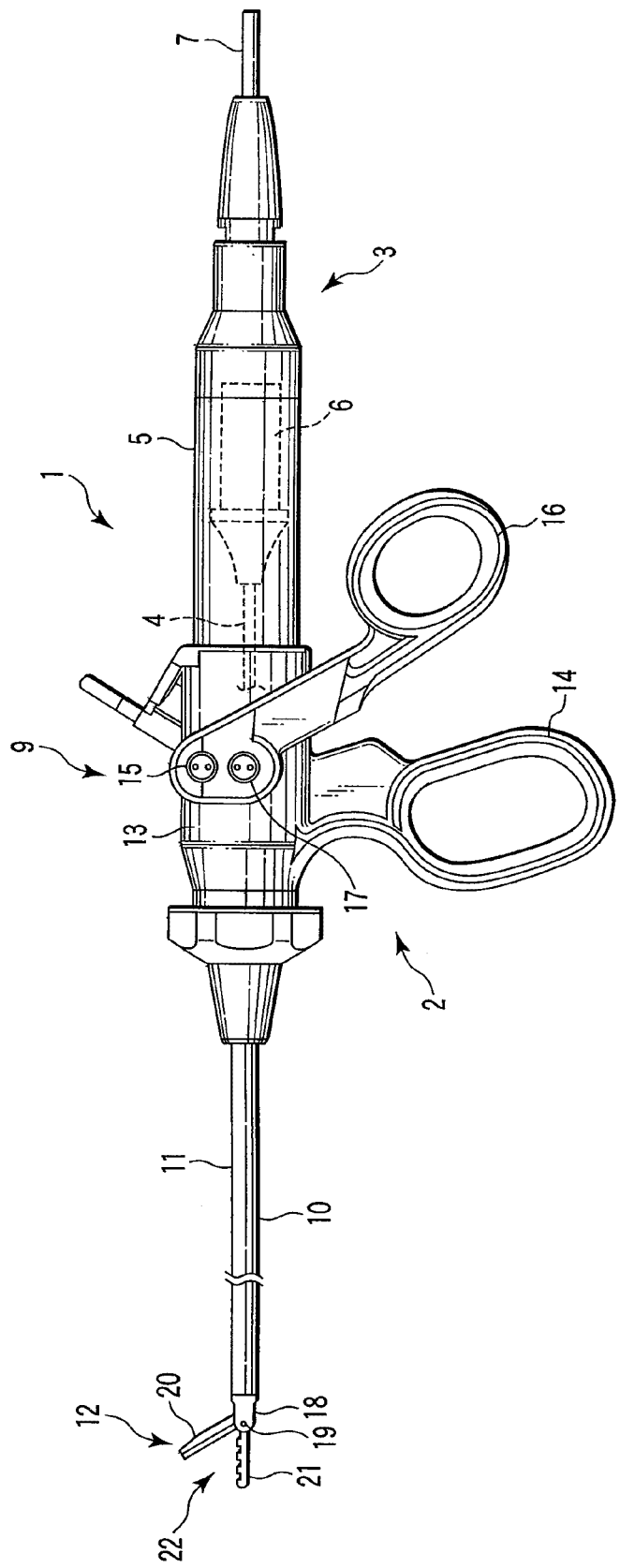
FIG. 1 is a side view showing a schematic configuration of a whole ultrasonic clotting and incising apparatus according to a first embodiment of the present invention.

A first embodiment of the present invention will be explained below with reference from FIGS. 1 to 5. FIG. 1 shows a schematic configuration of a whole ultrasonic clotting and incising apparatus 1 according to the first embodiment. The ultrasonic clotting and incising apparatus 1 mainly comprises a handle unit 2, a transducer unit 3, and an ultrasonic transmission member (probe) 4.

The transducer unit 3 includes a cylindrical cover 5. An ultrasonic transducer 6 is provided inside the cover 5. One end of a cable 7 is connected to a proximal end of the transducer unit 3. The other end of the cable 7 is connected to an ultrasonic wave power source apparatus (not shown). The ultrasonic transducer 6 is driven by supplying power from the ultrasonic wave power source to the ultrasonic transducer 6 via the cable 7.

The ultrasonic transmission member 4 is a rod-like member which transmits/amplitudes ultrasonic vibration produced at the ultrasonic transducer 6. A proximal end portion of the ultrasonic transmission member 4 includes a horn unit whose outer diameter gradually decreases toward a distal end side of the horn unit. The ultrasonic transmission member 4 is detachably connected to the ultrasonic transducer 6 by such means as a screw.

As shown in FIG. 1, the handle unit 2 is provided with an operation unit 9, an insertion sheath unit 11 comprising an elongated mantle pipe 10, and a distal end acting unit 12. A proximal end portion of the insertion sheath unit 11 is attached to the operation unit 9 rotatably in a spinning direction about an axis. The distal end acting unit 12 is provided at a distal end of the insertion sheath unit 11.

The operation unit 9 of the handle unit 2 includes an operation unit main body 13, a fixed handle 14, and a movable handle 16. The operation unit main body 13 is formed integrally with the fixed handle 14. The movable handle 16 is rotatably attached to the operation unit main body 13 via a handle pivoting shaft 15. A proximal end of the operation unit main body 13 is detachably connected with the transducer unit 3.

The movable handle 16 has an engagement pin 17. The engagement pin 17 is disposed near the handle pivoting shaft 15, and it is protruded into the operation unit main body 13. The engagement pin 17 is engaged with a slider mechanism (not shown) disposed inside the operation unit main body 13.

Figure 2:
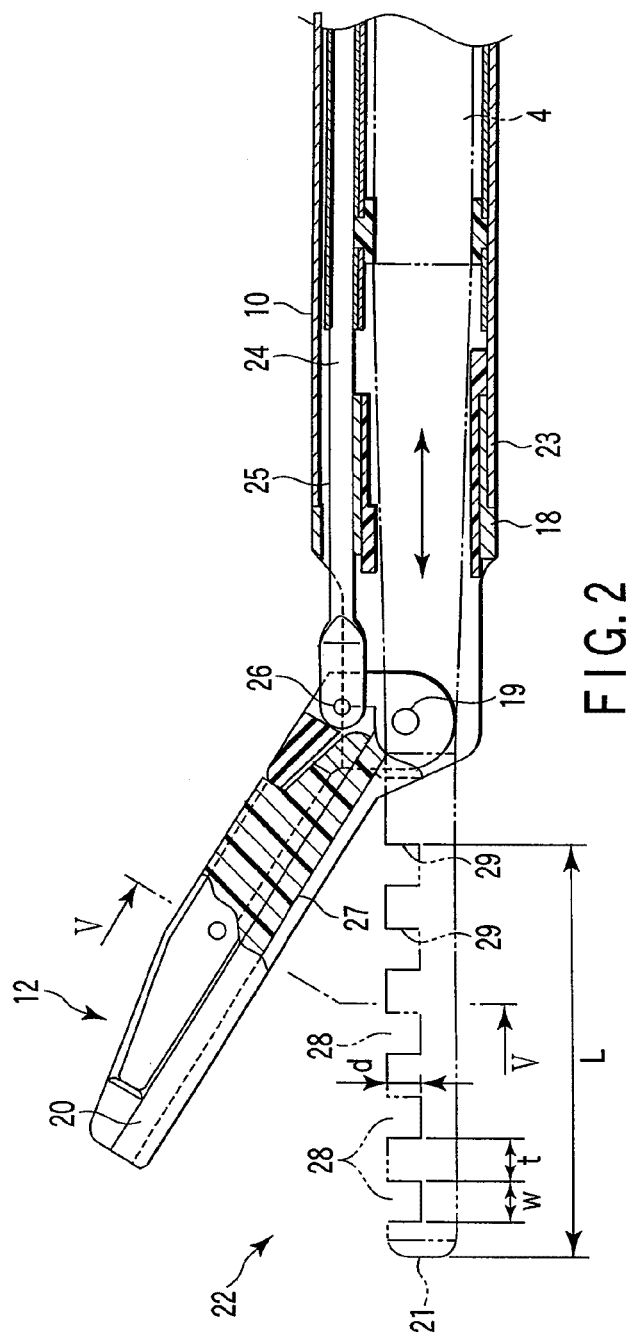
FIG. 2 is a vertical sectional view of a peripheral portion of a distal end acting unit of the ultrasonic clotting and incising apparatus according to the first embodiment in an enlarged manner.

FIG. 2 shows a peripheral portion of the distal end acting unit 12 of the handle unit 2. The distal end acting unit 12 of the handle unit 2 includes a holding member 18 and a grasping member 20 of one-side opening type. The holding member 18 is attached to a distal end portion of the mantle pipe 10. The grasping member 20 is rotatably attached to the holding member 18 via a pivoting shaft 19.

The distal end acting unit 12 together with the distal end portion 21 of the ultrasonic transmission member 4 configures a procedure unit 22 of the ultrasonic clopping and incising apparatus 1. The grasping member 20 of a one-side opening type can grasp a body tissue between the one and the distal end portion 21.

The holding member 18 is formed with a main channel 23 and a sub-channel 25. The ultrasonic transmission member 4 is inserted into the main channel 23. An operation rod 24 for operating the grasping member 20 in a rotating manner is inserted into the sub-channel 25.

As shown in FIG. 2, a distal end portion of the operation rod 24 is coupled to a proximal end of the grasping member 20 via a pivoting pin 26. A proximal end side of the operation rod 24 is coupled to a slider mechanism (not shown) disposed inside the operation unit main body 13. The operation rod 24 is caused to advance or retreat in the axial direction via the slider mechanism by rotating the movable handle 16. The grasping member 20 of the distal end acting unit 12 is opened or closed in a linking manner with advancing or retreating action of the operation rod 24 in the axial direction.

Figure 5:
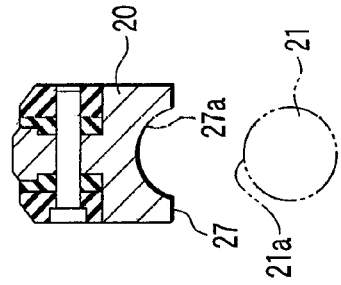
FIG. 5 is a sectional view showing a state that the grasping member has been separated from the distal end portion of the ultrasonic transmission member of the ultrasonic clotting and incising apparatus according to the first embodiment, taken along line V-V in FIG. 2.
Figure 4:
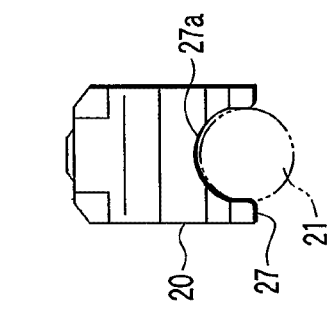
FIG. 4 is a front view showing a state that a distal end portion of the ultrasonic transmission member and a grasping member have meshed with each other in the ultrasonic clotting and incising apparatus according to the first embodiment.
Figure 3:
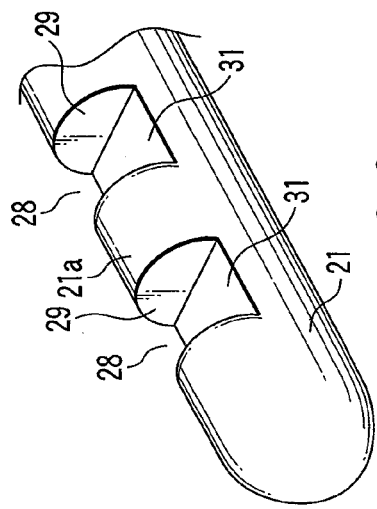
FIG. 3 is a perspective view showing a distal end portion of an ultrasonic transmission member of the ultrasonic clotting and incising apparatus according to the first embodiment.

A lower face (a face facing the distal end portion 21) of the grasping member 20 serves as a grasping face 27 grasping a tissue between the one and the distal end portion 21. As shown in FIG. 5, the grasping face 27 is formed with a recessed portion 27a with an arc shape in section. The arc-shaped section of the recessed portion 27a of the grasping face 27 is formed to conform with a shape of an outer peripheral face 21a of the distal end portion 21. Thereby, when the grasping member 20 is operated to be closed, as shown in FIG. 4, the distal end portion 21 of the ultrasonic transmission member 4 and the grasping member 20 is caused to mesh with each other in a state that the distal end portion 21 of the ultrasonic transmission member 4 is inserted into the recessed portion 27a of the grasping face 27.

A plurality of groove portions 28 is formed on a face of the distal end portion 21 of the ultrasonic transmission member 4 facing the grasping face 27. The sizes of the groove portions 28 in the present embodiment are as follows:

groove width (w)=1.2 mm
distance between grooves 28 (t)=1.2 mm
depth (d)=0.5 mm
length from distal end of the distal end portion 21 to the last groove portion 28(L)=12 mm
the number of groove portions 28: 5

It is desirable that the length from the distal end of the distal end portion 21 to the last groove portion 28 (L) is within $\lambda/8$. In general, vibration amplitude of the ultrasonic transmission member 4 lowers according to advancing thereof from a probe distal end to a node position at a proximal end side. When the vibration amplitude of the ultrasonic transmission member 4 advances from the distal end of the distal end portion 21 toward the proximal end side beyond $\lambda/8$, it becomes about 70% or less of amplitude at the distal end position. Therefore, when vibration amplitude advances from the distal end of the distal end portion 21 toward the proximal end side beyond $\lambda/8$, it is difficult to obtain sufficient procedure ability. In the present embodiment, a vibration frequency of ultrasonic wave transmitted to the ultrasonic transmission member 4 is 47 kHz, and one wavelength ($\lambda$) is 104 mm. Therefore, a length (L) from the distal end of the distal end portion 21 to the last groove portion 28 is 12 mm=$\lambda/8.7$. Each groove portion 28 is formed by perpendicular faces 29 which are front and rear wall faces and a horizontal face 31 of a bottom portion.

It is desirable that a width (w) of the groove portion 28 is in a range of $\lambda/200 \leq w \leq \lambda/16$. The present embodiment is directed to an ultrasonic clotting and incising apparatus 1 using not only frictional heat but also cavitation produced by vibration. Impact pressure due to the cavitation tends to be proportion to an area of the perpendicular face 29 to the vibration direction of ultrasonic wave transmitted to the ultrasonic transmission member 4. The total area of the perpendicular faces 29 increases according to increase in the number of groove portions 28. It is necessary to provide at least two groove portions 28 in order to use the cavitation effect. It is necessary to set the width (w) of the groove portion 28 to $\lambda/16$ or less in order to provide two groove portions 28 within the length (L)=$\lambda/8$ from the distal end of the distal end portion 21 to the last groove portion 28. In the present embodiment, it is necessary to set the width (w) of the groove portion 28 to less than 6.5 mm. On the other hand, when the number of groove portions 28 on the distal end portion 21 is increased excessively, the cavitation effect is raised but the width (w) of the groove portion 28 is reduced. In the present embodiment, $\lambda/200=0.52$ mm. When the groove portion 28 is further thin, there is a possibility that sufficient procedure ability cannot be obtained due to adhesion of a body tissue to an inner face of the groove portion 28.

It is desirable that a ratio d/w of the depth (d) and the width (w) of groove portion 28 is in a range of $0.1 \leq d/w \leq 5$. The area of the perpendicular face 29 increases according to increase of d/w. Thereby, the cavitation effect is elevated, but if the groove portion 28 becomes excessively deep relative to the width (w), a problem similar to the above-mentioned case that the groove portion 28 becomes thin, occurs. In the present embodiment, d/w is 0.42. In case of d/w=5, the width (w) becomes 0.4 mm, for example, in the depth (d)=2 mm. When the groove portion 28 becomes further deep relative to the width, there is a possibility that sufficient procedure ability cannot be obtained due to adhesion of a body tissue to the inner wall of the groove portion 28.

Next, an operation of the present embodiment will be explained. The distal end of the insertion sheath unit 11 is first inserted to a position near a targeted body tissue which is a procedure object at a time of using the ultrasonic clotting and incising apparatus 1 according to the present embodiment. Subsequently, the body tissue is positioned between the grasping member 20 and the distal end portion 21 of the ultrasonic transmission member 4. In this state, the movable handle 16 is operated in a closing direction in a rotating manner to grasp the body tissue between the grasping member 20 and the distal end portion 21.

In such a state of grasping the body tissue, power is supplied from the ultrasonic power source to the ultrasonic transducer 6 to vibrate the ultrasonic transducer 6. The ultrasonic vibration is transmitted to the distal end portion 21 of the ultrasonic transmission member 4. The body tissue contacting with the groove portions 28 at the distal end portion 21 is crushed by impact pressure of the cavitation produced from the groove portions 28. Simultaneously therewith, the body tissue is clotted by frictional heat produced by grasping the body tissue between the grasping member 20 and the distal end portion 21 of the ultrasonic transmission member 4.

The effect obtained by the present embodiment is as follows. That is, by providing the groove portions 28 at the distal end portion 21 of the ultrasonic transmission member 4, when a procedure such as incising, removing, or clotting of a body tissue is performed by using ultrasonic waves on the body tissue grasped between the grasping member 20 and the distal end portion 21, the procedure can be performed by using both cavitation and frictional heat. Therefore, since clotting and incising of a body tissue can be performed at a lower vibration velocity, risk of thermal damage can be reduced, so that an ultrasonic clotting and incising apparatus with high safety can be provided. Further, a stronger still procedure even to a site where risk of thermal damage does not occur can be conducted at a vibration velocity approximately equal to a conventional one.

The vertical wall face of the groove portion 28 is a perpendicular face 29 with an angle of 90° to the vibrating direction at the distal end portion 21 of the ultrasonic transmission member 4 according to the present embodiment, but the vertical wall face is not limited to this face. Cavitation produced by the groove portion 28 at the distal end portion 21 of the ultrasonic transmission member 4 is produced more easily according to the vertical wall face closer to a perpendicular face to the vibration direction. When the angle θ of the vertical wall face of the groove portion 28 is less than 70° to the vibration direction, a drag coefficient becomes about half or less of a drag coefficient obtained when the vertical wall face is a perpendicular face (90°). The drag coefficient shows magnitude of resistance occurring when the ultrasonic transmission member 4 moves in medium (for example, water). Since the resistance from the medium increases according to increase in drag coefficient, the cavitation is produced more easily. Therefore, it is desirable that the angle θ of the vertical wall face of the groove portion 28 is set from 70° to 90° to the vibration direction of ultrasonic wave to be transmitted to the ultrasonic transmission member 4. That is, the perpendicular face 29 of the groove portion 28 of the first embodiment can be changed to an inclined face put in a range of 70° to 90°, for example. By adopting the inclined face put in this range, a corresponding cavitation effect can be obtained. For example, there are modification examples shown in FIGS. 6 and 7.

FIG. 6 shows a first modification example of the distal end portion 21 of the ultrasonic transmission member 4 of the ultrasonic clotting and incising apparatus 1 according to the first embodiment. In the present modification example, a front side vertical wall face 28a1 of front and rear two vertical wall faces 28a1 and 28b1 of the groove portion 28 at the distal end portion 21 is formed by a perpendicular face 29 with an angle θ of 90°. The angle θ of the rear vertical wall face 28b1 is designed to be 75°.

FIG. 7 shows a second modification example of the distal end portion 21 of the ultrasonic transmission member 4 of the ultrasonic clotting and incising apparatus 1 according to the first embodiment. In the present modification example, angles θ of both of front and rear vertical wall faces 28a2, 28b2 of the groove portion 28 at the distal end portion 21 is defined by inclined faces with an angle θ of 75°.

In the shapes of the groove portions 28 like modification examples shown in FIGS. 6 and 7, impact pressure due to cavitation at the vertical wall face (the vertical wall face 28b1, 28a2, 28b2 of the inclined face with an angle of 75°) of the groove portion 28 is slightly reduced. However, in the modification examples shown in FIGS. 6 and 7, since a horizontal face 31 to the vibration direction as shown by arrow in FIG. 2 is not present, an even cavitation effect over the whole grasping face 27 can be expected.

Figure 9:
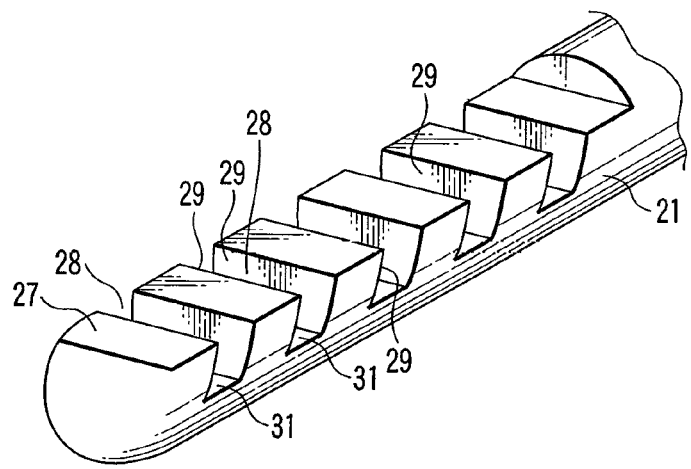
FIG. 9 is a perspective view showing a distal end portion of an ultrasonic transmission member of the ultrasonic clotting and incising apparatus according to the second embodiment.
Figure 10:
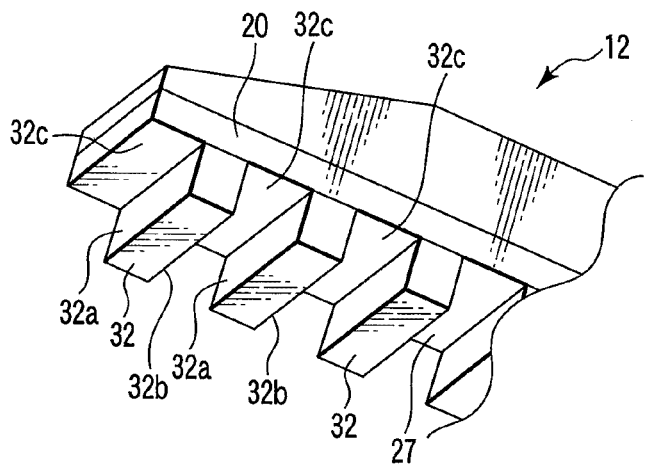
FIG. 10 is a perspective view showing a portion of a grasping face of a grasping member of the ultrasonic clotting and incising apparatus according to the second embodiment.

FIGS. 8 to 10 show a second embodiment of the present invention. In the present embodiment, the configuration of the grasping member 20 according to the first embodiment (FIGS. 1 to 5) has been change in the following manner. The remaining configuration of the second embodiment is similar to that of the first embodiment.

That is, in the second embodiment, as shown in FIG. 8, a plurality of protrusions 32 is formed on a grasping face 27 which is a lower face of the grasping member 20. The protrusions 32 are formed at positions corresponding to the groove portions 28 at the distal end portion 21 so as to have shapes corresponding to the shapes of the groove portions 28. As shown in FIG. 10, vertical wall faces 32a and 32b are formed at front portion and a rear portion of each protrusion 32. Further, a horizontal face 32c is formed on the bottom portions between adjacent protrusions 32.

The front and rear vertical wall faces 32a and 32b of respective protrusions 32 configure perpendicular faces with an angle θ of 90° to the horizontal face 32c of the grasping face 27. When movement is conducted such that the grasping member 20 and the distal end portion 21 are closed, the grasping member 20 and the distal end portion 21 are caused to mesh with each other without clearance in a state that the respective protrusions 32 of the grasping member 20 are inserted into the respective groove portions 28 at the distal end portion 21 of the ultrasonic transmission member 4.

Therefore, when movement is conducted such that the grasping member 20 and the distal end portion 21 are closed to grasp a small thin body tissue, for example, a blood vessel with a diameter Ø of 0.5 mm or less, incising/clotting can be conducted securely. The function/effect other than the above is similar to those in the first embodiment.

Figure 11:
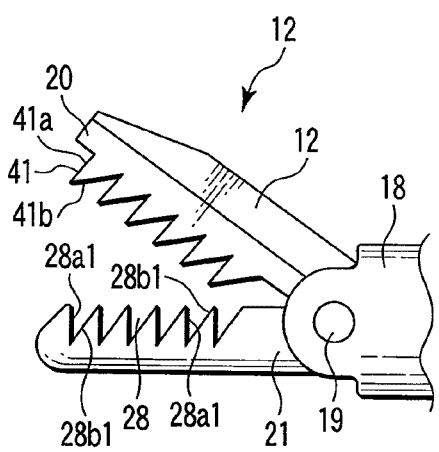
FIG. 11 is a side view showing a first modification example of the ultrasonic clotting and incising apparatus according to the second embodiment.

FIG. 11 shows a first modification example of the ultrasonic clotting and incising apparatus 1 according to the second embodiment. In the present modification example, a plurality of protrusions 41 is formed on a grasping face 27 which is a lower face of the grasping member 20 at positions corresponding to the groove portions 28 at the distal end portion 21 of the ultrasonic transmission member 4 shown in FIG. 6 to have shapes corresponding to shapes of the respective groove portions 28. Each protrusion 41 is formed with a perpendicular face 41a with an angle θ of 90° on a front vertical wall face. A rear vertical wall face is formed with an inclined face 41b with an angle θ of 75°.

In the present modification example, therefore, when movement is performed such that the grasping member 20 and the distal end portion 21 are closed, the grasping member 20 and the distal end portion 21 are caused to mesh with each other without clearance in a state that the respective protrusions 41 of the grasping member 20 are inserted into the respective groove portions 28 at the distal end portion 21 of the ultrasonic transmission member 4.

Figure 12:
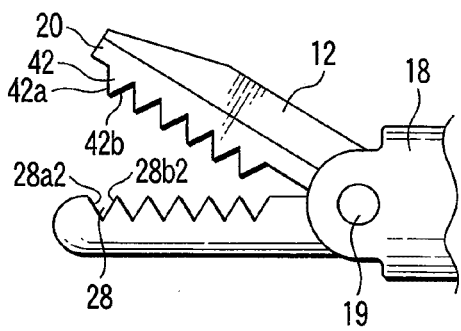
FIG. 12 is a side view showing a second modification example of the ultrasonic clotting and incising apparatus according to the second embodiment.

FIG. 12 shows a second modification example of the ultrasonic clopping and incising apparatus 1 according to the second embodiment. In the present modification example, a plurality of protrusions 42 is formed on a grasping face 27 which is a lower face of the grasping member 20 at positions corresponding to the groove portions 28 at the distal end portion 21 of the ultrasonic transmission member 4 shown in FIG. 7 so as to have shapes corresponding to those of the respective grooves 28. Each protrusion 42 is formed with an inclined face 42a with an angle θ of 75° on a front vertical wall face. A rear vertical wall face is also formed with an inclined face 42b with an angle θ of 75°.

In the present modification example, therefore, when movement is performed such that the grasping member 20 and the distal end portion 21 are closed, the grasping member 20 and the distal end portion 21 are caused to mesh with each other without clearance in a state that the respective protrusions 42 of the grasping member 20 are inserted into the respective groove portions 28 at the distal end portion 21 of the ultrasonic transmission member 4.

FIGS. 13 to 21C show a third embodiment of the present invention. An ultrasonic clotting and incising apparatus 51 shown in FIG. 14 comprises an elongated endoscope 52 and an ultrasonic procedure tool 53.

The endoscope 52 includes an elongated insertion unit 54. A proximal end of the insertion unit 54 is coupled with an operation unit (not shown). The insertion unit 54 is provided with an elongated flexible pipe portion (not shown), a flexible bending portion (not shown), and a distal end configuring portion 55. A plurality of bending pieces is provided on the bending portion in parallel.

Figures 13, 14:
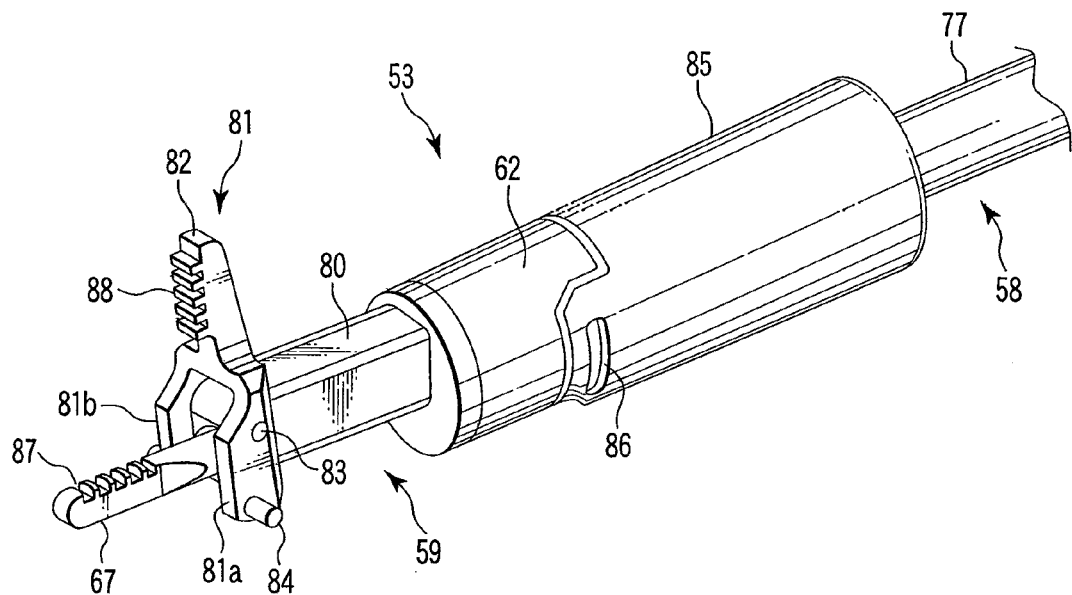
FIG. 13 is a perspective view showing a peripheral portion of a distal end acting unit of an ultrasonic clotting and incising apparatus according to a third embodiment of the present invention in an enlarged manner.
FIG. 14 is a vertical sectional view of a main portion showing a state that the ultrasonic clotting and incising apparatus according to the third embodiment has been inserted into a channel of an endoscope.

As shown in FIG. 14, the distal end configuring portion 55 is provided with an observation window 56 of an observation optical system, an illumination window (not shown) of the illumination optical system, an opening portion 57a communicating with a distal end portion of a procedure tool channel 57, and the like. An objective optical system is disposed on the observation window 56 of the observation optical system behind a cover glass. An imaging device such as an image guide fiber or a CCD is disposed at an imaging position of the objective optical system. One end portion of a signal cable is connected to the imaging device. A distal end portion of a light guide fiber is disposed in the illumination window behind the cover glass.

The signal cable of the imaging device, the light guide fiber, the procedure tool channel 57, a bending operation wire, and the like are extended to the operation unit side through inner space of the insertion unit 54. The signal cable of the imaging device, the light guide fiber, the procedure tool channel 57, the bending operation wire, and the like are accommodated in the inner space of the insertion unit 54 as inner parts. Observation of an affected area is made possible by picking up an observation image taken in from the observation window 56 by the imaging device in a state that illumination light has been emitted from the illumination window to light up a surrounding area of the observation window 56, converting the observation image to an electric signal and displaying the observation image on an external monitor or the like.

An operation knob (not shown) for operating the bending portion in a bending manner is disposed on the operation unit. The operation wire for driving the bending pieces on the bending portion is coupled to a bending operation mechanism (not shown). The distal end portion of the endoscope 52 can be bent by operating the bending portion in a bending manner according to operation of the operation knob.

FIG. 13 shows a peripheral portion of the distal end portion of the ultrasonic procedure tool 53 in an enlarged manner. The ultrasonic procedure tool 53 of the present embodiment includes a procedure tool main body 59 disposed at the distal end portion of the elongated flexible pipe portion 58. A procedure tool operation unit 60 shown in FIG. 18 is disposed at a proximal end portion of the flexible pipe portion 58.

Figures 15, 16, 17:
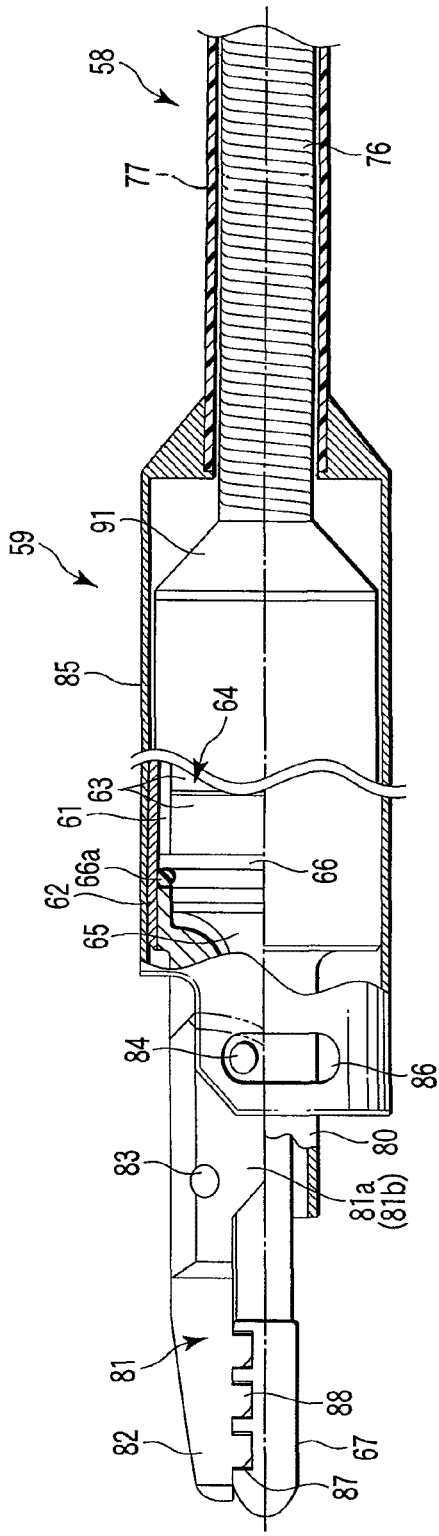
FIG. 15 is a side view showing a peripheral portion of the distal end acting unit of the ultrasonic clotting and incising apparatus according to the third embodiment in a partially sectioned manner.
FIG. 16 is a plan view showing a distal end portion of the distal end acting unit of the ultrasonic clotting and incising apparatus shown in FIG. 15 in a partially sectioned manner.
FIG. 17 is a side view showing a state that the distal end acting unit of the ultrasonic clotting and incising apparatus shown in FIG. 15 has been operated to be opened.
Figure 21A:
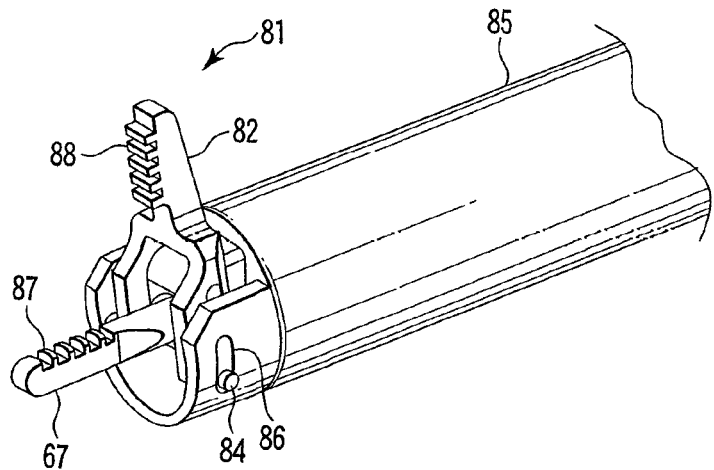
FIG. 21A is a perspective view showing a state that a grasping member of the ultrasonic clotting and incising apparatus according to the third embodiment has been operated to be opened.
Figure 21B:
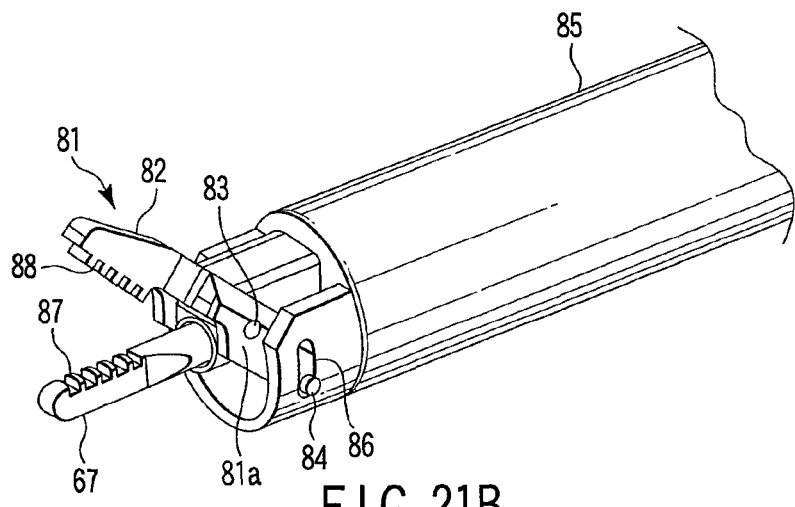
FIG. 21B is a perspective view showing a state that the grasping member of the ultrasonic clotting and incising apparatus according to the third embodiment is put in the course of opening operation thereof.
Figure 21C:
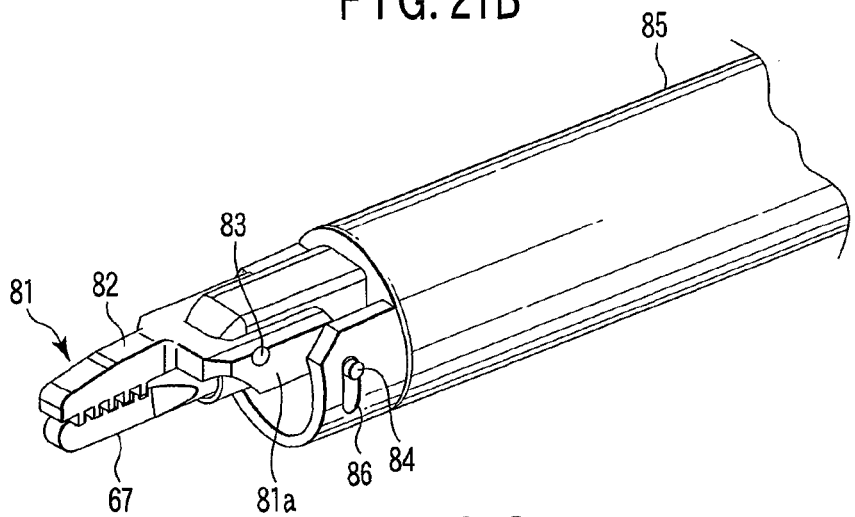
FIG. 21C is a perspective view showing a state that a grasping member of the ultrasonic clotting and incising apparatus according to the third embodiment has been operated to be closed.

As shown in FIG. 15, the procedure tool main body 59 includes an ultrasonic transducer 61. A periphery of the ultrasonic transducer 61 is covered with a cylindrical cylinder 62.

As shown in FIGS. 15 and 16, the ultrasonic transducer 61 includes an ultrasonic transducer main body 64 comprising a plurality of piezoelectric devices 63. A horn 65 with a narrowed shape for increasing vibration amplitude of the ultrasonic transducer 61 and a flange 66 are disposed at a distal end portion of the ultrasonic transducer main body 64. Further, a distal end portion of the horn 65 is extended forward so that a transducer distal end portion 67 is formed.

As shown in FIG. 19, a plus electrode 68 and a minus electrode 69 for supplying power to the piezoelectric devices 63 and a backing plate 70 are disposed at a rear end portion of the ultrasonic transducer main body 64. The piezoelectric devices 63 and the electrodes 68, 69 are sandwiched between the horn 65 and the backing plate 70.

A cylindrical inner cover 71 is disposed between the plus electrode 68 and the minus electrode 69, and the backing plate 70. The inner cover 71 is disposed between the plus electrode 68 and the minus electrode 69, and the backing plate 70. Thereby, the plus electrode 68 and the minus electrode 69 are prevented from being electrically short-circuited via the backing plate 70.

As shown in FIG. 19, the cylindrical inner cover 71 disposed inside the cylinder 62 has an inner diameter larger than the backing plate 70 of the transducer 61 and an entire length longer than the backing plate 70, and has an outer diameter smaller than an inner diameter of the cylinder 62.

As shown in FIG. 18, the procedure tool operation unit 60 comprises an operation unit main body 72, a movable handle 73, an ultrasonic wave connector 74, and a plug 75 for a radio knife. The ultrasonic wave connector 74 includes three terminals of an earth terminal 74a, a minus terminal 74b, and a plus terminal 74c, and it is connected to an external ultrasonic power source via a cable (not shown).

The flexible pipe portion 58 includes a flexible coil shaft 76 and an insulating outer tube 77. An outer periphery of the coil shaft 76 is covered with the outer tube 77. A plus wiring 78 and a minus wiring 79 are inserted into an inner space portion 76a of the coil shaft 76. A proximal end portion of the plus wiring 78 is connected to the plus terminal 74c of the ultrasonic wave connector 74 and a proximal end portion of the minus wiring 79 is connected to the minus terminal 74b of the ultrasonic wave connector 74. The earth terminal 74a of the ultrasonic wave connector 74 is electrically grounded. Therefore, the plus wiring 78 and the minus wiring 79 inserted into the inner space portion 76a of the coil shaft 76 can shield electrical noise from the outside of the coil shaft 76.

A proximal end portion of the coil shaft 76 is fixed to the operation unit main body 72. A distal end portion of the coil shaft 76 is fixed to a proximal end portion of a partition wall 91. A distal end portion of the partition wall 91 is attached to a rear end portion of the cylinder 62 in a fitting manner. Two wiring holes 92 and 93 are formed in the partition wall 91. The plus wiring 78 is inserted into one wiring hole 92 while the minus wiring 79 is inserted into the other wiring hole 93.

A distal end portion of the plus wiring 78 and a distal end portion of the minus wiring 79 are connected to the plus electrode 68 and the minus electrode 69 of the ultrasonic transducer main body 64, respectively. Power supplied from the ultrasonic power source is applied to the plus electrode 68 and the minus electrode 69 from the ultrasonic connector 74 of the operation unit 60 via the plus wiring 78 and the minus wiring 79. Thereby, the ultrasonic transducer 61 produces ultrasonic vibration. The ultrasonic vibration whose amplitude has been expanded by passing through the narrowed type horn 65 is transmitted to the transducer distal end portion 67. The flange 66 corresponds to a node position of vibration and it is fixed to the cylinder 62 via an O-ring 66a.

In the present embodiment, a distance from a distal end of the transducer distal end portion 67 to flange 66 is a quarter wavelength. A portion corresponding to the quarter wavelength is covered with a horn cover 80 fixed to the cylinder 62 except for the transducer distal end portion 67.

The entire length of the ultrasonic transducer 61 is half a wavelength. In the present embodiment, the ultrasonic transducer 61 produces ultrasonic vibration with 100 kHz. When ultrasonic vibration is produced by using resonance, one wavelength in high frequency is short, so that the entire length of the ultrasonic transducer 61 becomes short. When the endoscope 52 is used, if the entire length of the ultrasonic transducer 61 is long, the hard portion becomes long, so that it becomes difficult to bend the endoscope 52, which results in deterioration of operability of the endoscope 52. Therefore, it is required to set the entire length of the ultrasonic transducer 61 to 50 mm or less. In order to satisfy this requirement, the frequency of the ultrasonic vibration must be 75 kHz or more.

On the other hand, when the frequency of the ultrasonic vibration is 150 kHz, vibration velocity required for producing cavitation is about 2.5 times the vibration velocity at 100 kHz or it is about 5 times the vibration velocity at 20 kHz. It is difficult to obtain sufficient cavitation at a frequency exceeding 150 kHz.

Therefore, in order to achieve both high operability and procedure ability, it is ideal that the frequency of the ultrasonic vibration is set in a range of 75 to 150 kHz.

A grasping member 81 grasping a body tissue between the one and the transducer distal end portion 61 is provided at a distal end portion of the procedure tool main body 59. As shown in FIG. 16, the grasping member 81 comprises two supporting arms 81a, 81b and a grasping portion 82. Two supporting arm 81a, 81b are disposed on both sides of a distal end portion of the horn cover 80. Each of supporting arms 81a, 81b is provided with one rotating shaft 83 and two supporting pins 84. The supporting arms 81a, 81b of the grasping member 81 are rotatably pivoted to the horn cover 80 via the rotating shaft 83.

One of two supporting pins 84 is provided such that an inner end portion thereof is fixed to the supporting arm 81a while an outer end portion thereof projects outside the supporting arm 81a. Similarly, the other supporting pin 84 is provided such that an inner end portion thereof is fixed to the supporting arm 81b while an outer end portion thereof projects outside the supporting arm 81b.

A cylindrical distal end cover 85 is provided outside the cylinder 62 so as to cover the cylinder 62. The distal end cover 85 is supported so as to be movable relative to the cylinder 62 in an axial direction. As shown in FIG. 15, engagement holes 86 which are elongated long hole are provided on both side of the distal end portion of the distal end cover 85, respectively. Each engagement hole 86 is larger than the supporting pin 84 of the grasping member 81. Outer end portions of the supporting pins 84 are inserted into two engagement holes 86 of the distal end cover 85 in an engaging manner.

A proximal end portion of the distal end cover 85 is fixed to the distal end portion of the outer tube 77. A proximal end portion of the outer tube 77 is fixed to the movable handle 73. Thereby, the distal end cover 85 is moved in the axial direction via the outer tube 77 according to moving operation of the movable handle 73 in the axial direction to the operation unit main body 72. At this time, when the distal end cover 85 is moved backward and forward, the grasping member 81 is operated in an opening or closing manner about the rotating shaft 83 rotatably supported by the horn cover 80 (shown in FIGS. 21A, 21B, and 21C).

An outer diameter of the distal end cover 85 is smaller than an inner diameter of the channel 57 of the endoscope 52. Thereby, the ultrasonic procedure tool 53 is capable of advancing/retreating in the channel 57 and can be inserted into/removed from the channel 57.

A plurality of groove portions 87 is provided on a face of the transducer distal end portion 67 of the embodiment facing the grasping portion 82 of the grasping member 81. A desirable shape of the groove portion 87 is similar to that in the first embodiment. A plurality of protrusions 88 is formed on a grasping face 82a which is a lower face of the grasping portion 82 of the grasping member 81. The protrusions 88 of the grasping member 81 conform with the groove portions 87 of the transducer distal end portion 67 of the ultrasonic transducer 61. Incidentally, such a configuration can be adopted that the protrusions 88 are not provided on the grasping portion 82 when a targeted body tissue is material except for narrowed and thin material like the first embodiment.

In the present embodiment, excellent procedure ability can be obtained in the following two kinds of groove shapes (Example 1 and Example 2).

Example 1 groove width (w)=1 mm
distance between groove portions 87 (t)=0.2 mm
depth (d)=0.5 mm
length from a distal end of the transducer distal end portion 67 to the last groove portion 87 (L)=3.9 mm
the number of groove portions 87: 3
$\lambda$ (one wavelength) of ultrasonic vibration of the ultrasonic transducer 61 is 49 mm. Therefore, the length (L) from the distal end of the transducer distal end portion 67 to the last groove portion 87(L)=3.9 mm is $\lambda/12.6$, which falls within $\lambda/8$.

The width of the groove portion 87 (w)=1 mm is $\lambda/49$, which falls within a range of $\lambda/200 \leq w \leq \lambda/16$.

Ratio d/w of the depth (d) and the width (w) of the groove portion 87 is 0.5. This value falls within $0.1 \leq d/w \leq 5$.

Example 2 groove width (w)=0.4 mm
distance between groove portions 87 (t)=0.2 mm
depth (d)=0.5 mm
length from a distal end of the distal end portion 67 to the last groove portion 87 (L)=3.55 mm
the number of groove portions 87: 3
$\lambda$ (one wavelength) of ultrasonic vibration of the ultrasonic transducer 61 is 49 mm.

Therefore, the length from the distal end of the transducer distal end portion 67 to the last groove portion 87=3.55 mm is $\lambda/13.8$, which falls within $\lambda/8$.

The width of the groove portion 87 (w)=1 mm is $\lambda/122.5$, which falls within a range of $\lambda/200 \leq w \leq \lambda/16$. Ratio d/w of the depth (d) and the width (s) of the groove portion 87 is 1.25. This value falls within $0.1 \leq d/w \leq 5$.

Next, an operation of the present embodiment will be explained. The endoscope 52 shown in FIG. 14 is first inserted into a body cavity at a time of using the ultrasonic clotting and incising apparatus 51 of the present embodiment. At this time, an affected area is confirmed through the observation window 56 of the observation optical system.

Thereafter, the ultrasonic procedure tool 53 is inserted into the channel 57 of the endoscope 52. The distal end portion of the ultrasonic procedure tool 53 is caused to project outside the channel 57. Further, a body tissue is positioned between the grasping portion 82 of the grasping member 81 and the transducer distal end portion 67 of the transducer 61 while observation is being continued. In this state, the movable handle 73 is pulled so that the body tissue is grasped between the grasping portion 82 of the grasping member 81 and the transducer distal end portion 67.

In the state that the body tissue has been grasped in this manner, power is supplied to the ultrasonic transducer 61 from the ultrasonic power source so that ultrasonic transducer 61 is vibrated. The body tissue contacting with the groove portions 87 of the transducer distal end portion 67 is crushed by impact pressure of cavitation produced from the groove portions 87. Simultaneously therewith, the body tissue is clotted by frictional heat produced by grasping the body tissue. The operation other than the above is the same as that of the first embodiment.

In the present embodiment, sufficient incising/clotting of a body tissue such as a body organ and a digestive organ can be achieved even when the vibration velocity of the transducer distal end portion 67 is a low output such as 10 to 20 m/s.

The effect of the present embodiment is as follows. That is, by providing the groove portions 87 on the transducer distal end portion 67 of the ultrasonic transducer 61, an ultrasonic clotting and incising apparatus which can clot and incise tissue at a lower vibration velocity by using both cavitation and frictional heat can be provided.

Figure 22:
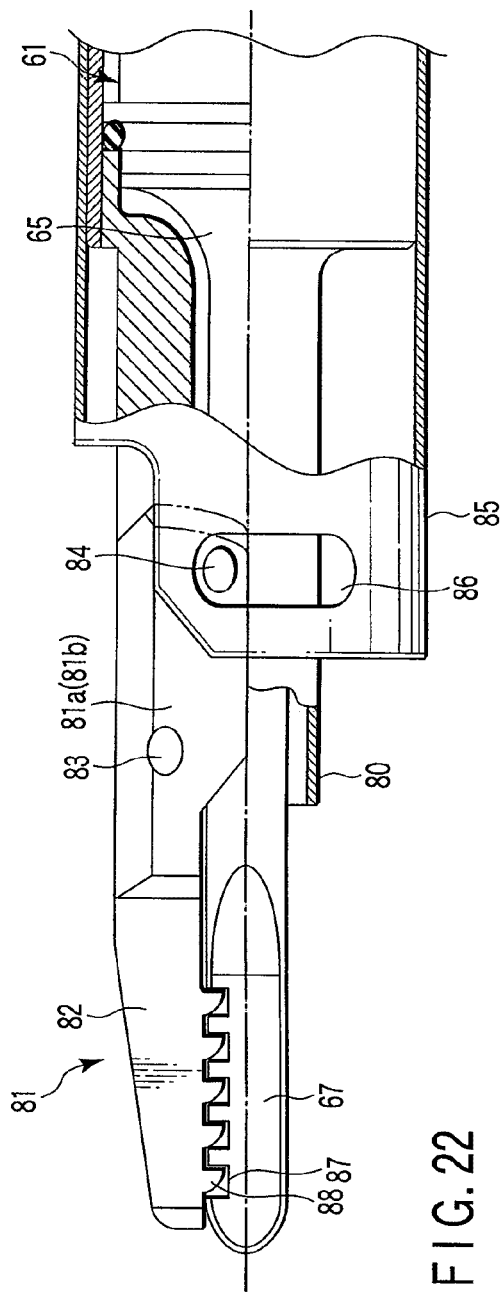
FIG. 22 is a side view showing a state that a grasping member of a first modification example of the distal end acting unit of the ultrasonic clotting and incising apparatus according to the third embodiment has been operated to be closed.
Figure 23:
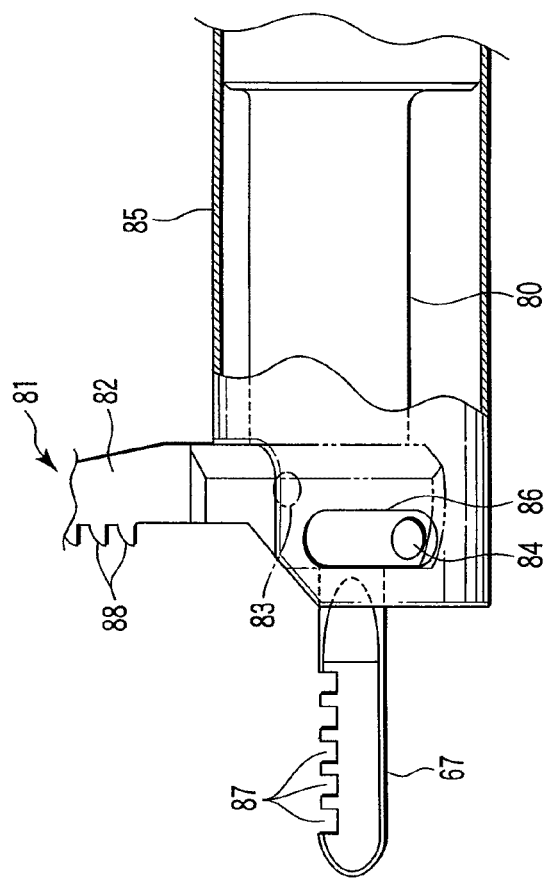
FIG. 23 is a side view showing a state that the grasping member of the first modification example of the distal end acting unit of the ultrasonic clotting and incising apparatus according to the third embodiment has been operated to be opened.

FIGS. 22 and 23 show a first modification example of the ultrasonic clotting and incising apparatus according to the third embodiment. FIG. 22 shows a state that the grasping member 81 has been closed. FIG. 23 shows a state that the grasping member 81 has been opened.

As shown in FIG. 22, even if one wall faces of the protrusions 88 of the grasping member 81 are faces inclined at an angle of less than 70°, when the other wall faces thereof have an inclined angle of 70° or more, some cavitation effect can be obtained.

Figure 24:
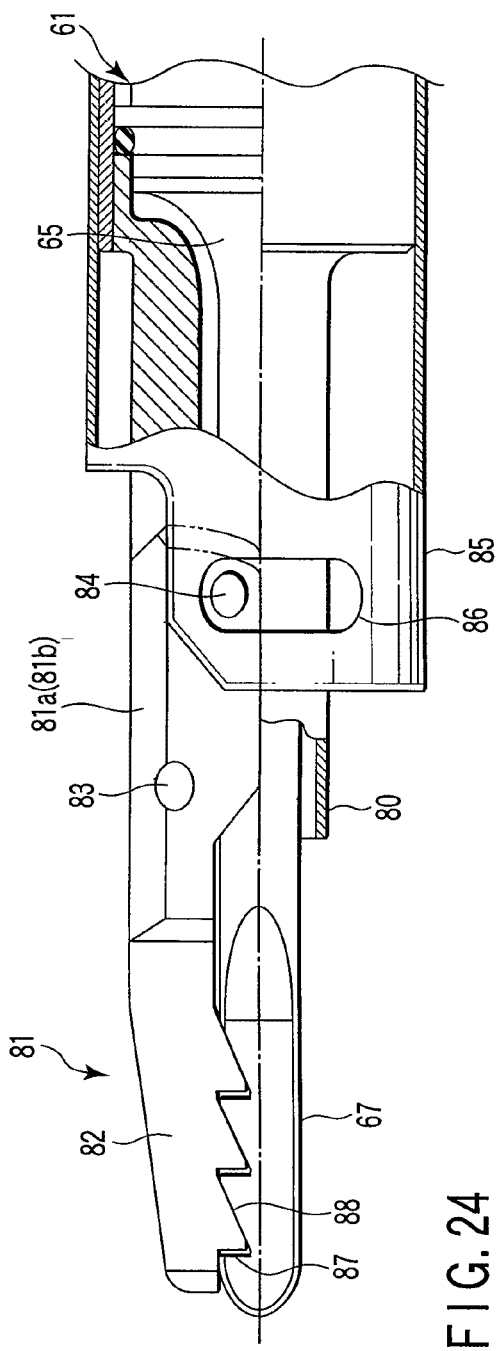
FIG. 24 is a side view showing a state that a grasping member of a second modification example of the distal end acting unit of the ultrasonic clotting and incising apparatus according to the third embodiment has been operated to be closed.
Figure 25:
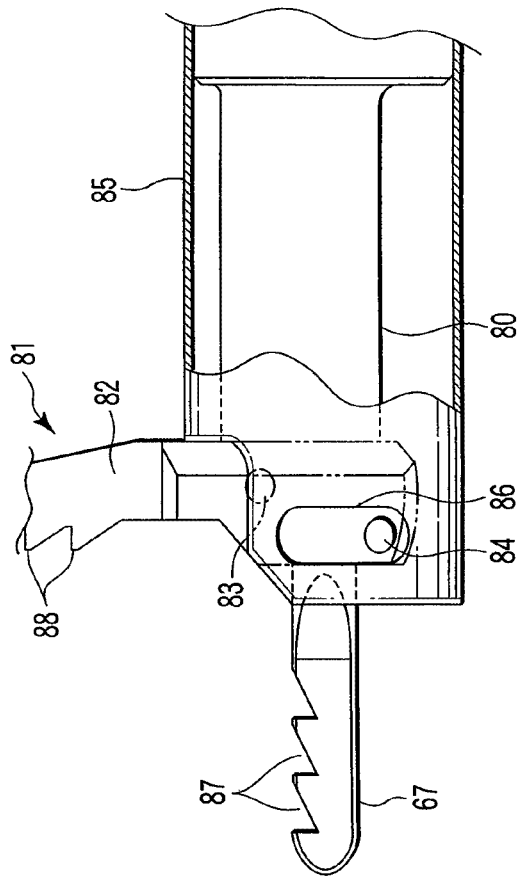

FIGS. 24 and 25 show a second modification example of the ultrasonic clotting and incising apparatus according to the third embodiment. A shape of the groove portions 87 at the transducer distal end portion 67 shown in FIG. 25 is as follows:

groove width (w)=1 mm
distance between groove portions 87 (t)=nothing
depth (d)=0.5 mm
length from a distal end of the transducer distal end portion 67 to the last groove portion 87 (L)=3.75 mm
the number of groove portions 87: 3
$\lambda$ (one wavelength) of ultrasonic vibration of the ultrasonic transducer 61 is 49 mm. Therefore, the length (L) from the distal end of the transducer distal end portion 67 to the last groove portion 87=3.75 mm is $\lambda/13.1$. This value falls within $\lambda/8$.

The width of the groove portion 87 (w)=1 mm is $\lambda/49$, which falls within a range of $\lambda/200 \leq w \leq \lambda/16$.

Ratio d/w of the depth (d) and the width (w) of the groove portion 87 is 0.5. This value falls within $0.1 \leq d/w \leq 5$.

Incidentally, such a configuration that only one supporting arm 81a, 81b of the grasping member 81 and only one engagement hole 86 of the distal end cover 85 are provided may be adopted. A groove portion 87 having a non-perpendicular face may be provided like the modification examples of the first embodiment shown in FIGS. 6 and 7.

Figure 26:
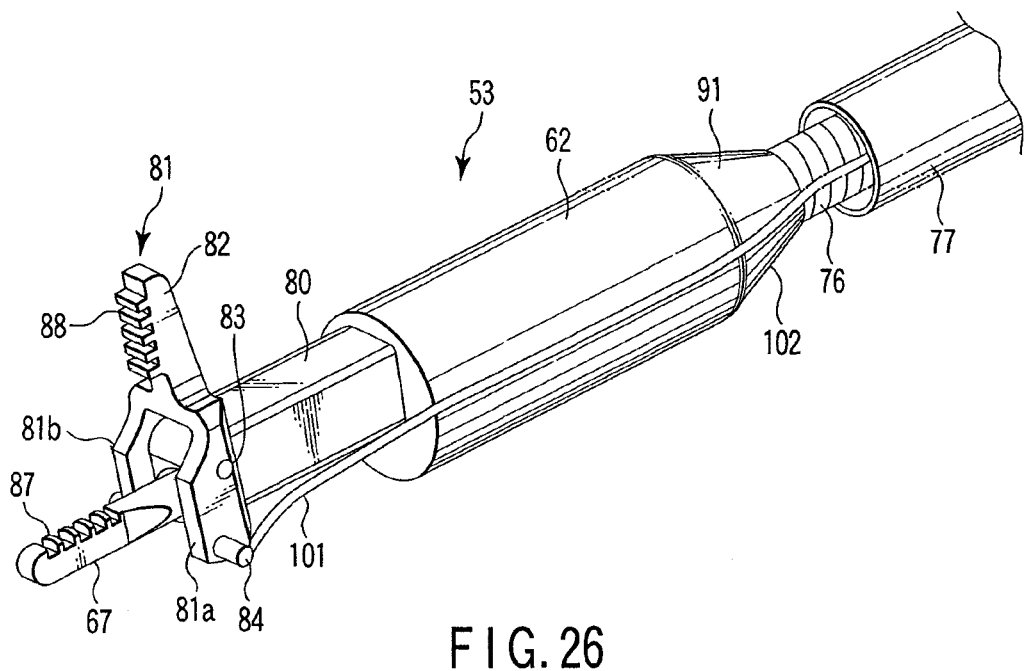
FIG. 26 is a perspective view showing a peripheral portion of a distal end acting unit of an ultrasonic clotting and incising apparatus according to a fourth embodiment of the present invention in an enlarged manner.
Figure 27:
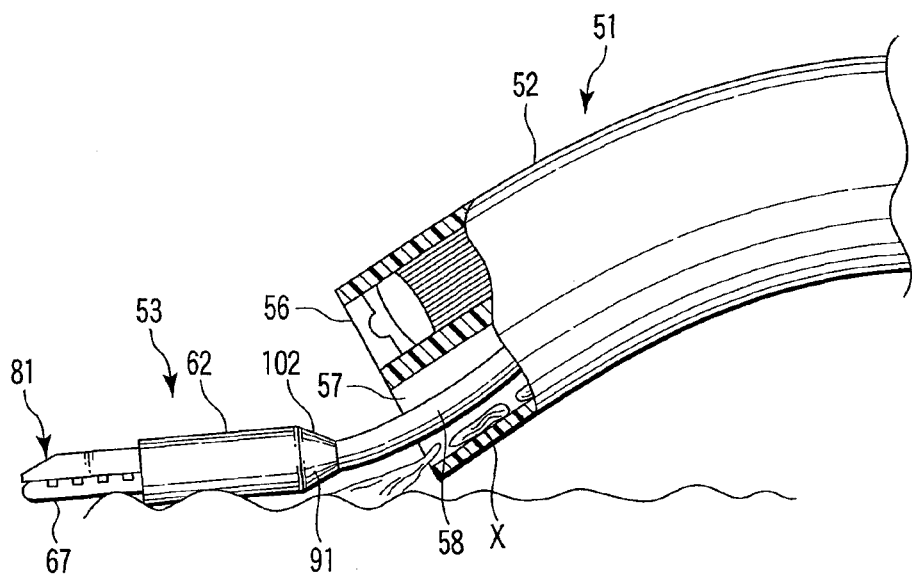
FIG. 27 is a side view showing a use state of the ultrasonic clotting and incising apparatus according to the fourth embodiment.

FIGS. 26 and 27 show a fourth embodiment of the present invention. In the present embodiment, an operation wire 101 is provided instead of the distal end cover 85 in the third embodiment (FIGS. 13 to 21C). As shown in FIG. 26, a distal end portion of the operation wire 101 is connected to a supporting pin 84 of a grasping member 81. A proximal end portion of the operation wire 101 is connected to the movable handle 73 of the operation unit 60 shown in FIG. 18.

A coil shaft 76 has a diameter smaller than that of the cylinder 62. A partition wall 91 is disposed between a proximal end portion of the cylinder 62 and a distal end portion of the coil shaft 76. A taper 102 is provided on the partition wall 91 between the coil shaft 76 and the cylinder 62. The configuration other than the above is the same as that in the third embodiment.

An operation/an effect of the present embodiment are as follows. That is, the endoscope shown in FIG. 27 is connected with a suction pump (not shown). A portion of the ultrasonic procedure tool 53 which is from the distal end thereof to the partition wall 91 is caused to project outside the channel 57 so that a clearance of the channel 57 is secured. Thereby, foreign material X can be sucked/drained from the channel 57 of the endoscope 52.

Here, when the foreign material X is clot of clotted blood, feces or the like, it can be sucked more easily by using the coil shaft 76 having a smaller diameter. When sucking/draining of the foreign material X are completed and the procedure tool 53 is pulled into the channel 57, a rear end portion of the partition wall 91 gets lodged on the distal end portion of the endoscope 52 unless the taper 102 is provided on the partition wall 91. Smooth taking-in and putting-out of the procedure tool 53 is made possible by providing the taper 102 on the partition wall 91.

Incidentally, the present invention is not limited to the embodiments and it can be implemented in variously modified manner without departing from the gist of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment instrument comprising:
   a piezoelectric element assembly which includes a plurality of piezoelectric elements which are aligned with a longitudinal direction, which includes one end and the other end and which is configured to generate ultrasonic vibration;
   a probe which includes a base end connected to the one end of the piezoelectric element assembly and a tip end extending from the proximal end along the longitudinal direction and which is configured to transmit the ultrasonic vibration from the base end to the tip end and treat a body tissue by the ultrasonic vibration;
   a backing plate which includes a distal end connected to the other end of the piezoelectric element assembly and a proximal end extending from the distal end of the backing plate along the longitudinal direction;
   an electrode assembly which is configured to extend from the distal end to the proximal end of the backing plate, which includes a plurality of electrodes respectively clamped between the piezoelectric elements and which is configured to electrify the piezoelectric elements and generate the ultrasonic vibration;
   a cylinder which is connected to the base end of the probe, which includes a toe end and a heel end and which is configured to locate the piezoelectric element assembly, the backing plate and the electrode assembly therein; and
   a cylindrical inner cover which includes an inner diameter larger than the backing plate and an outer diameter smaller than the cylinder;
   wherein:
   the inner cover is disposed between the backing plate and the electrode assembly, and
   the electrode assembly is disposed between the cylinder and the inner cover, wherein
   the cylinder includes a coil shaft having a diameter smaller than that of the cylinder and connected to the heel end of the cylinder; and
   the backing plate includes a taper with a smooth inclined face at a connecting portion with the coil shaft.

2. The ultrasonic treatment instrument according to claim 1, wherein the piezoelectric element assembly is configured to generate the ultrasonic vibration with a frequency of 100±25 kHz.

3. The ultrasonic treatment instrument according to claim 1, wherein
   the coil shaft includes an insulating outer tube covering an outer periphery thereof,
   the coil shaft is configured to insert a wire supplying power to the electrode assembly thereinto; and
   the coil shaft is electrically grounded.

* * * * *